United States Patent [19]
Bailey et al.

[11] Patent Number: 5,731,583
[45] Date of Patent: Mar. 24, 1998

[54] FOLDED OPTICAL PATH GAS ANALYZER WITH CYLINDRICAL CHOPPER

[75] Inventors: William D. Bailey, Arvada; Craig A. Patton, Boulder, both of Colo.

[73] Assignee: Ohmeda Inc., Liberty Corner, N.J.

[21] Appl. No.: 606,371

[22] Filed: Feb. 23, 1996

[51] Int. Cl.$^6$ .................................................. G01J 21/35
[52] U.S. Cl. ........................... 250/343; 250/345; 250/351
[58] Field of Search .................................. 250/345, 343, 250/351

[56] References Cited

U.S. PATENT DOCUMENTS

| | | | |
|---|---|---|---|
| 2,765,409 | 10/1956 | Hutchins et al. | 250/343 |
| 3,976,883 | 8/1976 | Krakow | 250/343 |
| 4,054,389 | 10/1977 | Owen | 356/189 |
| 4,157,470 | 6/1979 | Kotaka et al. | 250/345 |
| 4,158,772 | 6/1979 | Reedy | 250/338 |
| 4,180,734 | 12/1979 | Gedeon | 250/345 |
| 4,200,791 | 4/1980 | Burough | 250/343 |
| 4,467,203 | 8/1984 | Rappaport | 250/343 |
| 4,467,213 | 8/1984 | Farren | 250/504 R |
| 4,694,173 | 9/1987 | Wong | 250/343 |
| 4,888,484 | 12/1989 | Harvey | 250/343 |
| 4,914,719 | 4/1990 | Conlon et al. | 250/339 |
| 4,928,015 | 5/1990 | Butler et al. | 250/343 |
| 4,957,371 | 9/1990 | Pellicori et al. | 356/419 |
| 5,046,018 | 9/1991 | Flewelling et al. | 364/497 |
| 5,081,998 | 1/1992 | Yelderman et al. | 128/719 |
| 5,092,342 | 3/1992 | Hattendorff et al. | 128/719 |
| 5,166,755 | 11/1992 | Gat | 356/419 |
| 5,296,706 | 3/1994 | Braig et al. | 250/339 |
| 5,360,004 | 11/1994 | Purdy et al. | 128/633 |
| 5,379,764 | 1/1995 | Barnes et al. | 128/633 |
| 5,440,143 | 8/1995 | Carangelo et al. | 250/573 |
| 5,460,177 | 10/1995 | Purdy et al. | 128/633 |

FOREIGN PATENT DOCUMENTS

| | | | |
|---|---|---|---|
| 896736 | 5/1962 | United Kingdom | 250/343 |

OTHER PUBLICATIONS

George A. Martin, "Control of Product Quality by Plant-type Infrared Analyzers." *Instruments*, vol. 22 (Dec. 1949) pp. 1102–1105.

Maris et al., "Nonlinear Multicomponent Analysis by Infrared Spectrophotometry", pp. 1694–1703, 1983, *Anal. Chem.*, vol. 55, No. 11, September.

*Primary Examiner*—Constantine Hannaher
*Attorney, Agent, or Firm*—Roger M. Rathbun; William A. Schoneman; Thomas R. Marsh

[57] ABSTRACT

The disclosed gas analyzer (10) provides two separate folded optical paths (16 and 18) from a single source (12) to a single detector array (14) via a polychromatic filter (26). One optical path (16) passes through a sample gas chamber (24) containing a gas to be analyzed and the other path (18) passes through a reference chamber (30) containing a reference gas. On each optical path (16 or 18), radiation from the source (12) is collected by upstream optics (22 or 28) to form a converging beam (16b, c or 18b, c), thereby reducing or eliminating the need for collection optics at the detector array (14).

22 Claims, 6 Drawing Sheets

FOLDED OPTICAL PATH GAS ANALYZER WITH CYLINDRICAL CHOPPER

FIELD OF THE INVENTION

The present invention relates generally to spectral gas analyzers and, in particular, to a spectral gas analyzer for transmitting radiation on folded optical paths from a source to a filter/detector via sample and reference gas chambers according to a selected duty cycle. The invention is particularly apt for use with a linear variable filter/detector array to analyze the composition of respiratory and anesthetic gases.

BACKGROUND OF THE INVENTION

Gas analyzers are used in various medical and industrial applications to monitor the presence and concentration of selected components in a gaseous sample. In the medical context, gas analyzers are used to monitor the delivery of anesthesia by analyzing a respiratory stream with respect to selected respiratory and anesthetic components. In this regard, it may be desired to monitor respiratory gases such as oxygen and carbon dioxide, and one or more analgesic/anesthetic agents such as nitrous oxide, halothane and isoflurane. Monitoring anesthesia may therefore involve analyzing the respiratory stream with respect to one or multiple components.

Spectral gas analyzers provide an indication of the presence and concentration of selected components in a gas sample based on the detected spectral composition of radiation transmitted through the gas sample. The gaseous components of interest can be characterized with regard to specific radiation absorption properties. For example, a particular gaseous component may be characterized by an absorption band at a particular wavelength or wavelength range. By comparing the intensity of transmitted and received radiation of a selected wavelength for a particular gas sample, information regarding the absorption characteristics and composition of the sample can be obtained. To monitor multiple gaseous components, some spectral gas analyzers employ multiple radiation sources, multiple optical filters and/or multiple radiation detectors.

Potential sources of error in such analyzers include variations in source intensity or spectral output, variations relating to the optics and optical path between the source and detector and variations in detector response. Some of these variations are attributable to difference between multiple system components (e.g., multiple sources or detectors) or performance variations for a single component over time, and others are attributable to environmental factors such as changes in ambient temperature. It will be appreciated that minimizing such sources of potential error is crucial in many applications such as monitoring respiratory and anesthetic gases.

In addition to eliminating sources of error, it is desirable to limit the number of active components such as radiation source and receiver components, thereby simplifying analyzer design, reducing costs, reducing power requirements and heat production, and increasing reliability. Moreover, for many applications where space is limited, it is desirable to reduce analyzer size.

SUMMARY OF THE INVENTION

The present invention is directed to a spectral gas analyzer with a reduced number of active system components that provides accurate gas sample analysis, including multiple component or polychromatic analysis of respiratory/anesthetic gases. The invention reduces sources of potential error, reduces size and power requirements and enhances accuracy and reliability.

The inventive gas analyzer may include a chamber for containing a gas sample to be analyzed, means for transmitting a polychromatic radiation beam through the gas sample, means for filtering the polychromatic beam to yield two or more wavelength band portions, and means for separately detecting the wavelength band portions to provide information based on the intensity of radiation in the corresponding wavelength bands. The filtering means preferably includes a linear variable filter for providing varying wavelength response characteristics across the beamwidth. In order to separately detect the intensity of the wavelength band portions, the detector means preferably comprises an array of detector elements for providing information with respect to each bandwidth portion. The beam preferably defines an incidence angle relative to the filter means and detector means that is within a range of about 15° of normal in order to reduce spectral smearing.

According to one aspect of the present invention, a converging radiation beam is transmitted from a source side of a sample chamber through the sample chamber to directly impinge on a detector, thereby reducing or eliminating the need for detector side collection optics. A gas analyzer constructed according to this aspect of the invention includes a radiation source on one side of the sample chamber, a radiation detector on the opposite side of the sample chamber, and collection optics on the source side of the sample chamber for collecting radiation from the source to form a converging beam which is directed at the detector via or through the sample chamber. A filter, preferably a linear variable filter, can be employed in conjunction with the detector to allow for multiple component or polychromatic analysis. In this manner, radiation from an oppositely located source is directly received by a filter and detector upon exiting a sample chamber, thereby reducing detector side components and space requirements and reducing downstream optical losses.

According to another aspect of the present invention, two optical paths are provided from a single radiation source to a single radiation detector. One of the optical paths passes through a sample chamber containing the gas to be analyzed. Radiation transmitted by the other path is used as a reference and may be directed through a chamber that is evacuated, exposed to the ambient environment or contains a sample having a known gaseous composition. Radiation transmitted from the source to the detector via the reference path provides valuable optical performance information for use in accurately determining the composition of the gas under analysis. Preferably, the source is located upstream from the gas chambers and is thermally shielded from heat sensitive optical and detector elements and the gas samples to reduce undesirable heat related variances.

According to a still further aspect of the present invention, an optical chopper is provided to permit selective transmission of radiation from a single source via two optical paths according to a selected duty cycle. Each of the optical paths is defined in part by an optical element, such as a lens or mirror, that receives radiation from the source. The optical chopper includes a moveable radiation mask having at least one opening to allow passage of radiation. Each of the optical paths includes an optical element positioned so that the respective elements are spaced at least about 90° apart relative to the source. More preferably, the respective optical elements and source are about 180° apart, i.e., substantially collinear. Additionally, the mask is preferably provided in the form of a rotatable cylinder positioned around the source. The cylinder provides a degree of heat insulation in addition to optical masking. The operation of the chopper can be coordinated with cycling of a detector to achieve a desired sampling rate or duty cycle.

In one embodiment, a dual folded optical path gas analyzer with a cylindrical chopper is provided for use in analyzing respiratory and anesthetic gases. The analyzer includes an infrared radiation source disposed within a rotatable cylindrical chopper having at least one slit formed in a side wall thereof. Due to rotation of the cylindrical chopper, radiation passing through the slit(s) is alternately transmitted on separate sample and reference paths. Each path includes a spherical mirror for collecting radiation from the source to form a converging beam. On the sample path, the converging beam passes through a chamber containing a circulated sample of respiratory and anesthetic gases. The converging beam of the reference path passes through a chamber that contains a known gaseous composition. The optical paths are configured so that each of the converging beams passes through a linear variable filter and impinges on a single column detector array upon exiting the respective chambers. The readout from the detector array provides information concerning multiple components of the gas sample.

The present invention reduces the number of active gas analyzer components while allowing for dual optical path, polychromatic gas analysis of anesthetic/respiratory gases. In addition, the invention reduces or eliminates the need for collection optics at the detector and facilitates efficient and variable duty cycle usage. The gas analyzer of the present invention thereby reduces undesired variances and enhances accuracy and reliability. Finally, the invention constrains the incident angle of the alternating sample and reference convergent beams onto the detector array, thereby reducing spectral smearing.

BRIEF DESCRIPTION OF THE DRAWINGS

For a more complete understanding of the present invention and further advantages thereof, reference is now made to the following detailed description, taken in conjunction with the drawings, in which.

DETAILED DESCRIPTION

The gas analyzer of the present invention is useful in a variety of contexts where it is desired to analyze a gas sample with respect to the presence and/or concentration of one or more gaseous components. The analyzer configuration, selected wavelengths and various other factors may be varied depending on space requirements, the transmissivity/absorption characteristics of the gaseous components(s) of interest and the like. In the following description, the invention is set forth with respect to a specific embodiment for analyzing respiratory and anesthetic gases.

Figure 1:
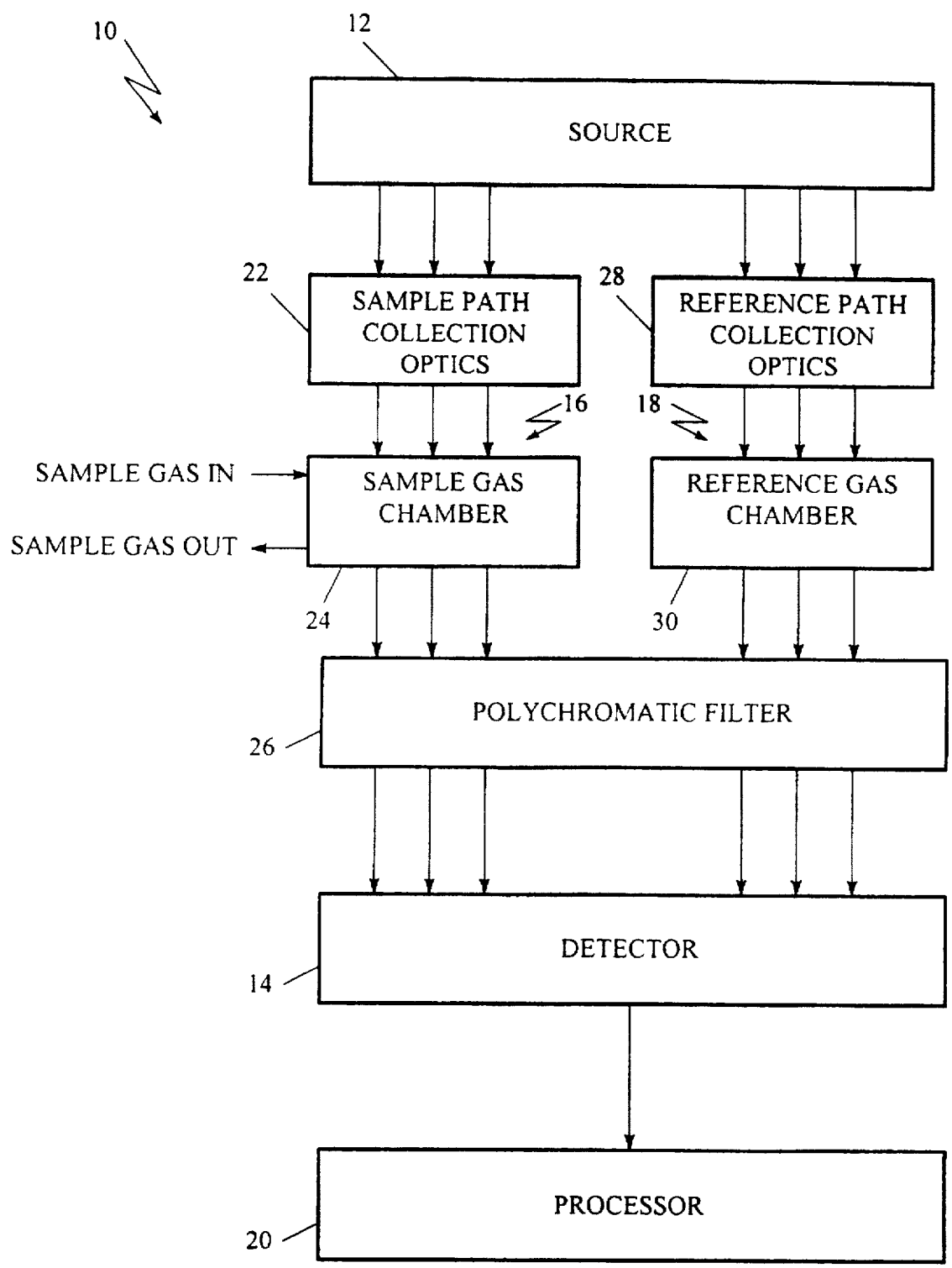
FIG. 1 is a schematic diagram illustrating a method of operation according to the present invention.

FIG. 1 is a schematic diagram illustrating the operation of a gas analyzer 10 according to the present invention. Generally, the gas analyzer comprises a radiation source 12, a detector assembly 15 including polychromatic filter 26 and a radiation detector 14, first (sample) 16 and second (reference) 18 optical paths between the source 12 and detector array 14, and a processor 20. On the sample path 16, radiation from source 12 is collected by sample path collection optics 22 to form a converging beam. The beam passes through sample gas chamber 24 and polychromatic filter 26 before impinging upon detector array 14. During operation, a continuous stream of respiratory and anesthetic gases is circulated through sample gas chamber 24 by gas inlet and outlet ports as shown. On the reference path 18, radiation from the source 12 is collected by reference path collection optics 28 to form a converging beam which is directed at detector array 14 via reference gas chamber 30 and filter 26.

A number of preferred operational aspects of the invention are illustrated by the schematic of FIG. 1. The illustrated analyzer 10 employs a single source 12 and single detector array 14, thereby reducing undesired variances and size requirements. This configuration is implemented using folded optical paths as described below. However, it will be appreciated that various aspects of the invention can be implemented without this preferred configuration.

FIG. 1 also shows the preferred dual optical path operation of the present invention. In order to accurately determine the radiation absorption characteristics and, hence, the composition of a gas sample, it is useful to obtain a reference measurement under circumstances similar to the sample measurement. Such a reference measurement is useful for calibration purposes, to compensate for any system variances and to facilitate digital processing. The reference measurement involves irradiating a reference gas chamber 30 that is evacuated, open to the ambient environment of the gas analyzer unit or includes a known gaseous composition so as to yield information for determining the concentration of components of the sample gas.

The system as illustrated in FIG. 1 also utilizes a polychromatic filter 26 in conjunction with a detector array 14 to allow for analysis of the incident radiation at multiple wavelengths or wavelength bands. The filter 26 is preferably located downstream from chambers 24 and 30 proximate to the detector array 14 as shown. The wavelength dependent transmission characteristics of the filter 26 can be selected to allow for analysis at wavelengths where the gaseous components of interest have a pronounced absorption band or other identifying characteristic. The output from a particular element or pixel of the detector array 14 associated with a particular filter element at a given time can therefore yield information concerning a specific gaseous component of interest. It will thus be appreciated that the illustrated system provides polychromatic analysis without the need to employ multiple detectors or to sequentially position multiple filters in the radiation path.

The detector array 14 may comprise a single column array of radiation sensitive elements, (e.g., a pyroelectric detector array,) for providing an electrical representation of the received radiation signal. The output information from the detector array 14, including reference readings and sample readings, is utilized by processor 20 to determine sample gas composition information by employing processing techniques such as digital subtraction and absorption/transmissivity algorithms. The processor 20 can then display information regarding the presence and concentration of one or more gaseous components as desired on a substantially real-time basis, thereby allowing an anesthesiologist or technician to carefully monitor a patient's condition.

Figure 2:
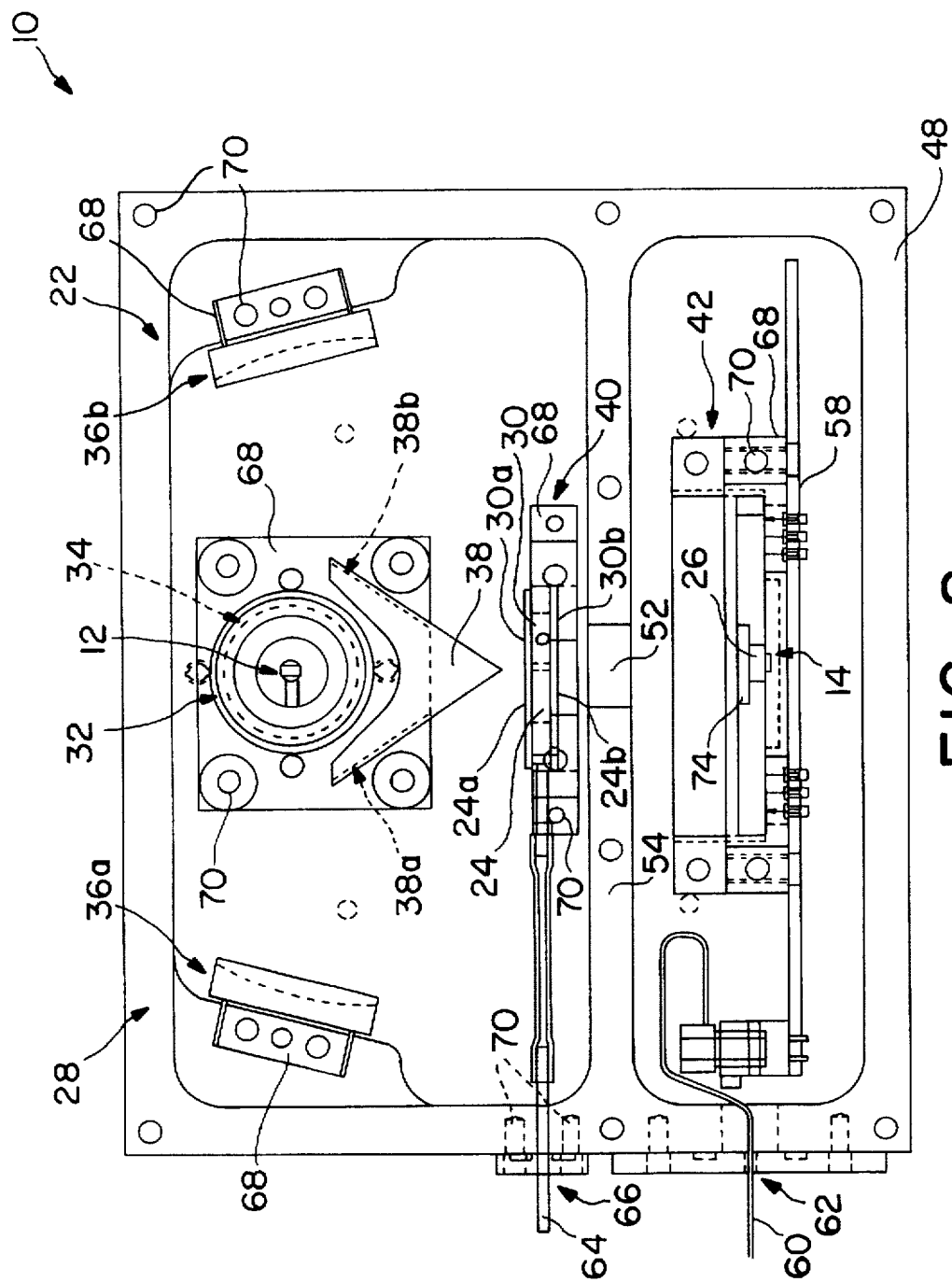
FIG. 2 is a top view of a gas analyzer according to the present invention.
Figure 4:
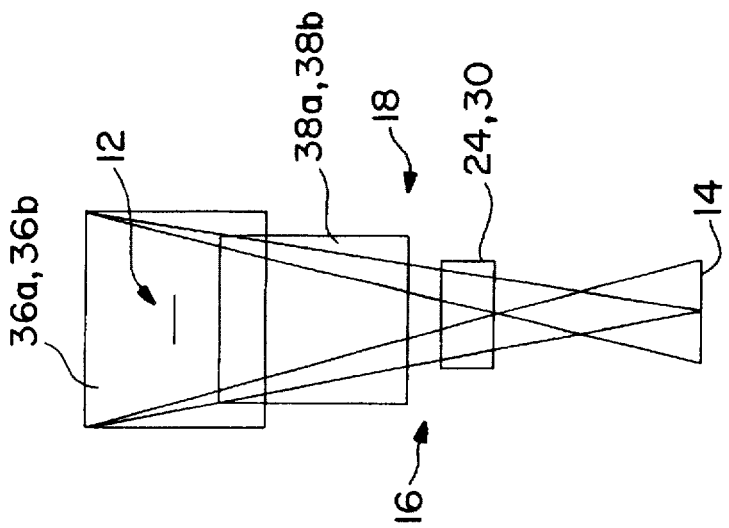
FIG. 4 is a side view illustrating optical pathways of the gas analyzer of FIG. 2.
Figure 3:
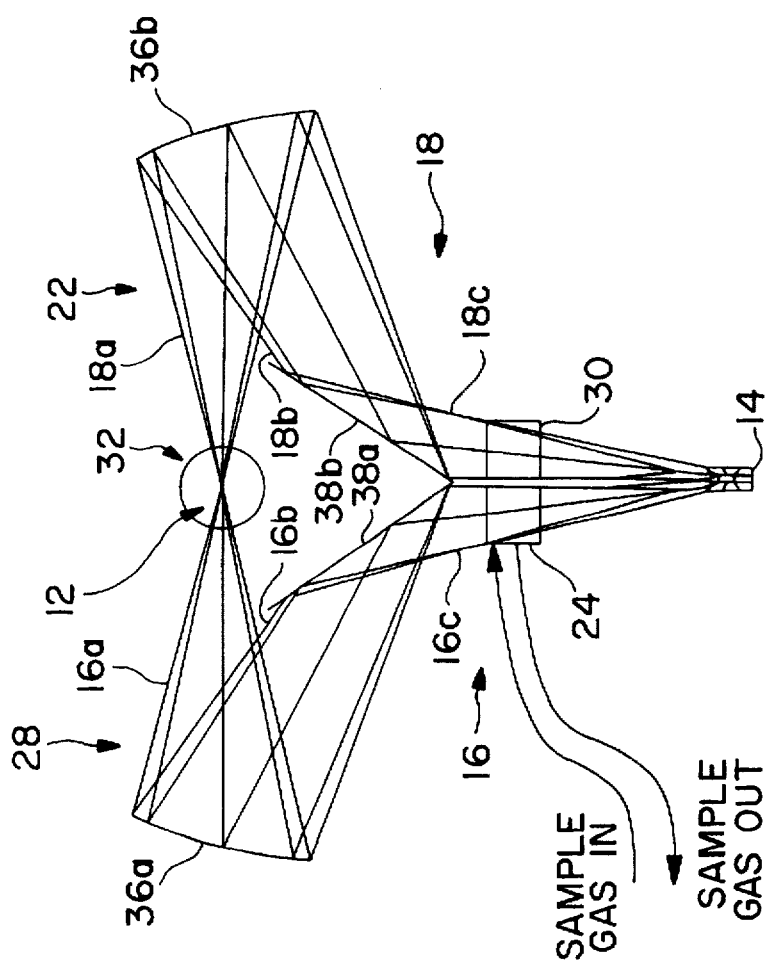
FIG. 3 is a top schematic view illustrating optical pathways of the gas analyzer of FIG. 2.
Figure 5A:
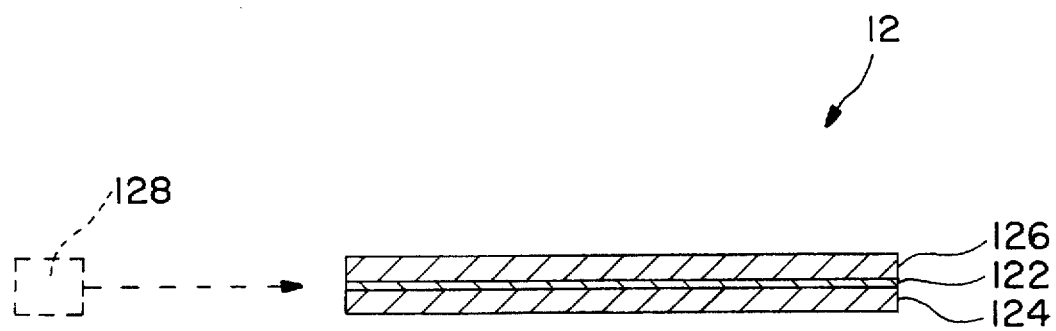
FIGS. 5a and 5b are side and bottom views, respectively, of the source of the gas analyzer of FIG. 2.
Figure 5B:
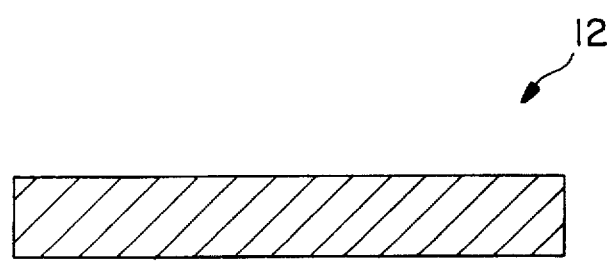
Figure 6:
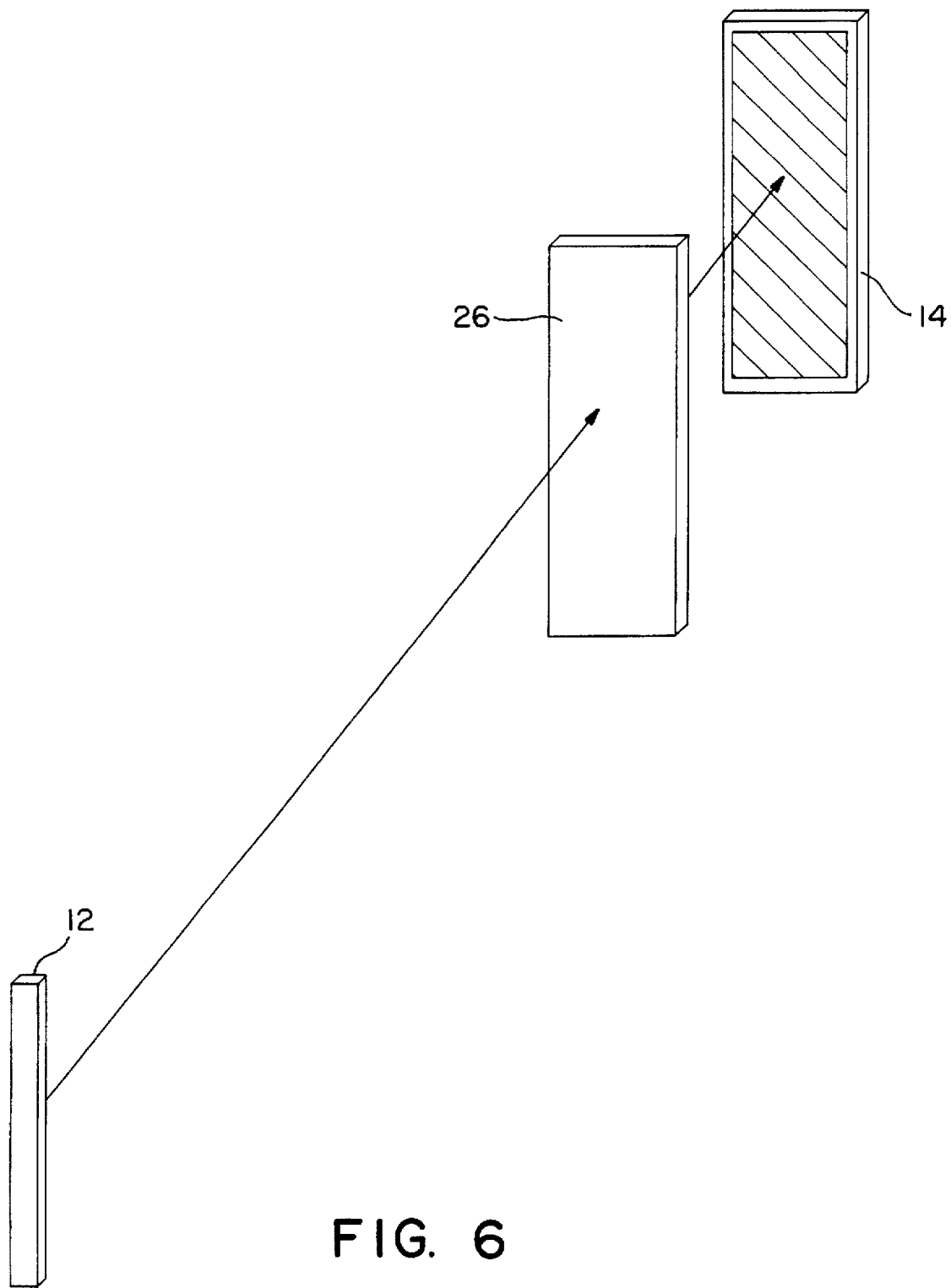
FIG. 6 is a schematic front perspective view showing radiation imaged on the filter/detector assembly of the gas analyzer of FIG. 2.
Figure 7:
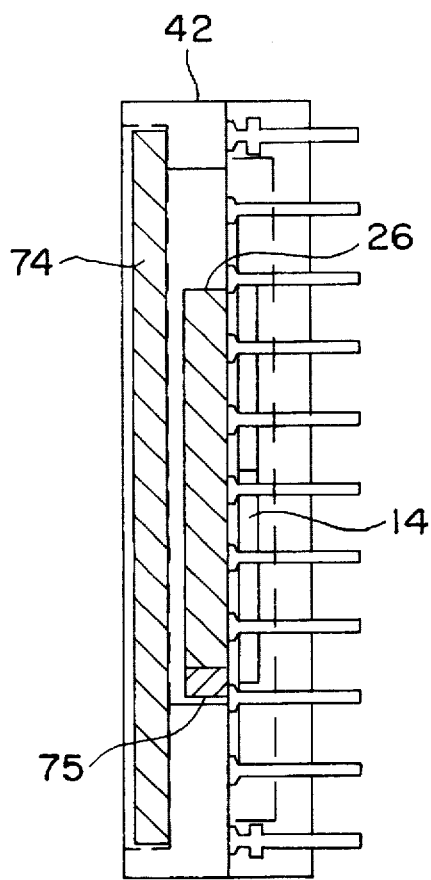
FIG. 7 is a side view of the filter/detector assembly of the gas analyzer of FIG. 2.

Referring to FIGS. 2–7, a folded optical path implementation of the gas analyzer 10 is illustrated. FIG. 2 illustrates various system components in detail and FIGS. 3 and 4 show optical schematics for the analyzer 10. FIGS. 5a and 5b show side and bottom views respectively of the source 12. FIGS. 6–7 show details of the filter/detector assembly 42 of the gas analyzer 10.

Generally, the gas analyzer 10 includes an upstanding infrared radiation source 12 positioned within a concentric, rotatable, cylindrical beam chopper 32 having at least one pass-through window or slit 34 in a portion of the side wall thereof, two spherical mirrors 36a, 36b, a flat mirror block 38 having flat mirrors 38a, 38b, a dual gas chamber member 40 having a sample gas chamber 24 and a reference gas chamber 30, and a filter/detector assembly 42 having polychromatic filter 26 and detector 14, all mounted within frame 48. As shown in the optical path schematics in FIGS. 3–4, the infrared source 12 emits radiation which, by virtue of the rotation of the chopper 32, results in the alternate impingement of beams 16a and 18a on spherical mirrors 36a and 36b, respectively. In turn, convergent beams 16b and 18b respectively reflect off spherical mirrors 36a and 36b and impinge on flat mirror elements 38a and 38b. The reflected infrared beams 16c and 18c then irradiate sample gas chamber 24 and reference gas chamber 30, respectively, before impinging on detector array 14. The optics are designed so that the source 12 is imaged on the detector array 14 as shown in FIG. 6 where the shaded area on detector array 14 represents the imaged source radiation. That is, the radiation is focused by the optics to define an image of the source 12 on the detector array 14. As shown, the detector array is thereby substantially completely illuminated and source energy losses are minimized. In this regard, in the illustrated embodiment, the source 12, filter 26 and array 14 are arranged in an aligned upstanding orientation.

The illustrated source 12 irradiates optical paths 16 and 18 with radiation encompassing a characteristic absorption band of at least one respiratory/anesthetic component of interest. Although various wavelengths or spectra can be employed including infrared (IR), visible and ultraviolet wavelength ranges, the illustrated source 12 is a polychromatic (black body) IR source transmitting radiation encompassing, for example, radiation in about the 4–12 micrometer wavelength range, which includes strong absorption bands of several respiratory/anesthetic components (e.g., within the 7–10 micrometer wavelength band).

The source 12, as shown in FIGS. 5a and 5b, is constructed in the form of an elongate, substantially homogeneous strip. As described below, the detector of the illustrated system is comprised of a columnar array of detector elements, e.g., a 1 by N array. The detector array is employed in conjunction with a polychromatic filter 26 so that the array elements provide intensity detection for multiple wavelengths or wavelength bands across a desired spectral range (e.g., the 7–10 micrometer wavelength band). The elongate, homogeneous source 12, in combination with the illustrated imaging optics, allows complete, substantially even and intense illumination of the detector array 14 for enhanced polychromatic analysis.

The source 12 includes a heater element 122 sandwiched between emitter plates 124 and 126. The heater element 122, which can be any suitable electrical resistance element, is preferably screened onto one of the plates 124 or 126 which serves as a substrate, although separate resistance wires may be employed. The illustrated plates 124 and 126 are constructed from black silicon nitride and are about 3 to 3.5 mm wide with a length of approximately 12 mm. The leads to the illustrated heating element are connected to a power source directly through the substrate silicon nitride plate 124 or 126. In order to provide the desired illumination, the source is preferably operated at a temperature greater than 900° C. The illustrated source 12 may be powered by a 100V rms source and reaches a temperature of approximately 1200° C. Operation in the preferred ranges has been found to provide an improved signal to noise ratio and improved overall performance in the context of the illustrated high frequency chopped optical path gas analyzer 10.

The source 12 is mounted within cylindrical beam chopper 32. The rotatable beam chopper 32 alternately transmits radiation from source 12 via the sample 16 and reference 18 optical paths and also contains, to an extent, heat generated by the source 12. The illustrated chopper 32 includes a single slit 34 in its cylindrical sidewall. Additionally, as shown, the source 12 and the spherical mirrors 36a and 36b are geometrically arranged in a substantially linear relationship. That is, the mirrors 36a and 36b are located about 180° apart relative to the source 12. It will be appreciated that the illustrated arrangement allows for convenient variable duty cycle usage by appropriate chopper operation and detector cycling. For example, the chopper 32 of the illustrated embodiment can be operated at 20 revolutions per second. In this regard, the detector array 14 can be read out at intervals coordinated with the rotation rate of the chopper 32.

The geometric arrangement of spherical mirrors 36a, 36b, flat mirrors 38a, 38b, and chambers 24, 30, defines the optical paths 16, 18 such that the beam incidence angles on the polychromatic filter 26 are nearly normal. In order to enhance operation of the filter/detector 42, it is preferred that incidence angles be much less than 30°–35° from normal (e.g., the angle that would be obtained if radiation was reflected directly from the spherical mirrors 36a, 36b to the detector 14 without intervening flat mirrors 38a, 38b). More preferably, the incidence angles are less than about 15° from normal to reduce spectral smearing. In the illustrated embodiment, as shown most clearly in FIGS. 3–4, the limit incidence angles are less than about 15° from normal, e.g., about 10° for centrally located pixels of the detector array and 14° for outer pixels, all within filter specifications.

Referring to FIGS. 2 and 7, after irradiating chambers 24 and 30, converging beams 16c, 18c pass through transparent window 52 in thermal isolation wall 54 of structural frame 48 and filter 26 and impinge upon detector array 14. A band pass filter 74 may be positioned in front of the polychromatic filter 26 to selectively pass radiation in the wavelength range of interest. In addition, a separate filter 75 (shown in FIG. 6 but not in FIG. 1), such as a sapphire $CO_2$ filter, may be positioned in adjacent, stacked relation to the polychromatic filter 26 for use in analyzing a specific component. Filter 26, as discussed above, is a polychromatic filter including multiple sections that are selective for multiple wavelengths or wavelength ranges of interest. In this regard, the filter 26 can be formed as an array of bandpass filters arranged side-by-side in the beampaths. More preferably, the filter comprises a linear variable filter that provides substantially linearly varying wavelength response characteristics across a beamwidth. Such a filter can be formed by depositing a stack of alternating high and low index of refraction materials on a filter substrate, where the stack layers are tapered in a controlled manner to yield the desired wavelength response variation. The illustrated filter provides substantially linearly varying wavelength response across, for example, the approximately 7–10 micrometer wavelength range.

The illustrated detector array 14 includes a single column of pyroelectric or heat sensitive elements and is supported by a detector board 58 carrying the circuitry for reading out the detector array 14, e.g., serial clocking circuits. The read out clocking of the detector array 14 can be readily coordinated with the chopper 32 rotation rate to provide alternate sample and reference values. In this regard, the 180° spacing of the spherical mirrors 36a and 36b relative to the source 12 allows for convenient interval clocking. Such coordination may be accomplished, for example, by indexing the read out clocking to pulses from an encoder or motor associated with the chopper 32. It will thus be appreciated that specific elements of the array 14 are associated with specific wavelength bands of filter 26. A polychromatic analysis of an incident beam can therefore be obtained by correlating the output from a particular element, or group thereof, and the associated wavelength band. This information can be used by the processor 20 (FIG. 1) to determine gaseous composition information pertaining to multiple gaseous components.

FIG. 2 also shows: electrical wires 60 and associated housing pass-through 62 for interconnecting the detector array 14 to a processor; gas inlet tubes 64 and an associated housing pass-through 66 for supplying a sample gas to the chamber 24; and various mounts 68 and mounting holes 70 for mounting the various system components within frame 48 or interconnection to related housings. Although not shown, it will be appreciated that sample chamber 24 communicates with a supply of respiratory/anesthetic gases by way of appropriate fluid flow control devices.

The illustrated gas analyzer thus provides a polychromatic analysis of multiple gaseous components in a respiratory/anesthetic sample by employing a single source, single detector array and polychromatic filter unit interrelated by folded optical paths. The collection optics are disposed upstream from the gas chamber so that beams exiting the gas chambers are directly received by the filter/detector. The chopper provides convenient duty cycle selection for alternate irradiation of the symmetrical reference and sample paths.

While various embodiments of the present invention have been described in detail, it is apparent that further modifications and adaptations of the invention will occur to those skilled in the art. However, it is to be expressly understood that such modifications and adaptations are within the spirit and scope of the present invention.

We claim:

1. A gas analyzer, comprising:
    a gas sample chamber;
    a radiation source disposed on a first side of said gas sample chamber;
    radiation detector means, disposed on a second side of said gas chamber opposite said first side, for detecting incident radiation; and
    first optical collection means, disposed on said first side of said gas sample chamber, for collecting radiation from said radiation source to form a converging radiation beam and for directing said converging beam through said chamber means so as to impinge upon said radiation detector means, including:
    a curved mirror for receiving radiation from the radiation source and reflecting a converging beam along a first axis; and
    a flat mirror for redirecting said converging beam along a second axis, wherein said first and second axes define an oblique angle therebetween.

2. The gas analyzer of claim 1, wherein said first collection means defines a first radiation pathway from said radiation source to said detector means and said gas analyzer further comprises means for defining a second radiation pathway, different than said first radiation pathway from said radiation source to said detector means.

3. The gas analyzer of claim 2, further comprising a reference chamber wherein said second radiation pathway passes through a second chamber.

4. The gas analyzer of claim 2, wherein a first overall length of said first pathway from said radiation source to said detector means is substantially the same as a second overall length of said second pathway from said radiation source to said detector means.

5. The gas analyzer of claim 2, wherein said means for defining a second radiation pathway comprises second optical collection means for collecting radiation from said radiation source so as to form a second converging radiation beam and for directing said second converging radiation beam to said detector means, wherein each of said first converging radiation beam and said second converging radiation beam define an incidence angle relative to a normal axis of said detector means of less than about 15°.

6. The gas analyzer of claim 2, further comprising chopper means for selectively transmitting radiation from said radiation source to said detector means via one of said first and second radiation pathways.

7. The gas analyzer of claim 6, wherein said chopper means comprises means for defining a duty cycle wherein radiation is transmitted via said first radiation pathway during a first series of time intervals and radiation is transmitted via said second radiation pathway during a second series of time intervals different than said first series of time intervals.

8. The gas analyzer of claim 7, further comprising means for coordinating operation of said radiation detector means to said duty cycle.

9. The gas analyzer of claim 6, wherein said chopper means comprises a moveable radiation shield, disposed between said radiation source and each of said first optical collection means and said means for defining a second radiation pathway.

10. The gas analyzer of claim 1, further comprising a housing for said source means including at least one opening for allowing passage of radiation from said source means therethrough, said housing being rotatable relative to said source means so as to permit transmission of radiation from said source means in various angular directions via said opening.

11. The gas analyzer of claim 1, wherein said detector means comprises a polychromatic filter and detector array.

12. A gas analyzer, comprising:
    a gas sample chamber;
    a radiation source;
    a radiation detector including an array of radiation sensitive elements;
    a radiation filter disposed between said source and detector for selectively filtering radiation from said source in a spatially distributed manner; and optical means for defining two separate optical paths from said source to said detector, each said path passing through said radiation filter and impinging on common elements of said array of said detector and one of said paths passing through said sample chamber, wherein each of said optical paths defines an incidence angle with respect to said filter of less than about 15° relative to normal, and wherein said optical paths at least partially overlap at said radiation detector.

13. The gas analyzer of claim 12, wherein said optical means comprises a curved mirror and a flat mirror.

14. The gas analyzer of claim 12, wherein said source and optical means are located on a first side of said gas sample chamber and detector is located on a second side of said gas sample chamber opposite said first side.

15. The gas analyzer of claim 12, further comprising chopper means for selectively transmitting radiation via said first and second optical paths.

16. The gas analyzer of claim 15, wherein said chopper means comprises a radiation shield having a window formed therein, wherein radiation is selectively transmitted via said first and second optical paths using said window.

17. A gas analyzer, comprising:

a gas sample chamber;

a reference gas chamber;

a radiation source;

a radiation detector;

first optical means for defining a first optical path for a first converging beam between said source and said detector, said first optical path passing through said gas sample chamber;

second optical means for defining a second optical path for a second converging beam between said source and said detector, said second optical path passing through said reference gas chamber; and chopper means for alternately transmitting said first and second converging beams via said first and second optical paths, respectively, from said source to said detector, said chopper means including a moveable radiation shield having a window formed therethrough, said window allowing alternate passage of radiation through said shield to said first and second optical paths, wherein said first and second optical path are alternately illuminated.

18. The gas analyzer of claim 17, wherein said shield comprises a rotatable housing disposed about said source and said window comprises a slit formed in said rotatable housing.

19. The gas analyzer of claim 17, wherein said detector is located on a first side of a gas sample chamber and said source, first and second optical means and said chopper means are located on a second side of said gas sample chamber opposite said first side.

20. The gas analyzer of claim 17, further comprising a radiation filter located so that radiation transmitted via each of said first and second optical paths passes through said filter.

21. The gas analyzer of claim 20, wherein said filter comprises a polychromatic filter.

22. A method for analyzing a gas sample comprising the steps of:

transmitting radiation from a radiation source to a radiation detector via a first optical path, transmitting radiation from said radiation source to said radiation detector via a second optical path;

alternately collecting radiation from said source to form first and second converging beams on said first and second optical paths, respectively;

passing said first converging beam through a gas sample; and passing said second converging beam through a reference gas;

disposing a radiation detector on said first and second optical paths; and employing said detector to directly receive said first and second converging beams transmitted through said gas sample and reference gas, respectively, wherein said detector provides information regarding a composition of said sample gas.

* * * * *